United States Patent
Hansmann et al.

(10) Patent No.: US 10,898,671 B2
(45) Date of Patent: Jan. 26, 2021

(54) METHOD AND DEVICE FOR THE ADAPTIVE REGULATION OF A POSITIVE END-EXPIRATORY PRESSURE (PEEP)

(71) Applicant: Drägerwerk AG & Co. KGaA, Lübeck (DE)

(72) Inventors: Hans-Ullrich Hansmann, Barnitz (DE); Karsten Hiltawsky, Stockelsdorf (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 366 days.

(21) Appl. No.: 15/793,201

(22) Filed: Oct. 25, 2017

(65) Prior Publication Data
US 2018/0110957 A1   Apr. 26, 2018

(30) Foreign Application Priority Data
Oct. 25, 2016   (DE) .......................... 10 2016 012 824

(51) Int. Cl.
*A61M 16/20* (2006.01)
*A61B 5/087* (2006.01)
(Continued)

(52) U.S. Cl.
CPC ............. *A61M 16/20* (2013.01); *A61B 5/087* (2013.01); *A61B 5/091* (2013.01);
(Continued)

(58) Field of Classification Search
CPC .. A61M 16/20; A61M 16/009; A61M 16/205; A61M 16/18; A61M 16/22; A61M 16/0833; A61M 2016/0027; A61M 2016/0021; A61M 2016/003; A61M 2016/0036; A61M 2016/0039; A61M 2016/0042; A61M 2016/0413;
(Continued)

(56) References Cited

U.S. PATENT DOCUMENTS 5,063,925 A * 11/1991 Frank .................... A61M 16/20
                                                      128/204.18
5,357,946 A   10/1994 Kee et al.
(Continued)

FOREIGN PATENT DOCUMENTS

| CN | 102369036 A | 3/2012 |
|---|---|---|
| CN | 105899249 A | 8/2016 |
| DE | 10 2011 106 406 A1 | 1/2013 |

*Primary Examiner* — Kendra D Carter
*Assistant Examiner* — Paige Kathleen Bugg
(74) *Attorney, Agent, or Firm* — McGlew and Tuttle, P.C.

(57) ABSTRACT

A method controls an expiratory gas flow at a user interface (16) of a ventilator (1) wherein the user interface (16) has an exhalation valve (11), which provides a positive end-expiratory pressure (PEEP). The method includes the following steps during a phase of exhalation: changing the positive end-expiratory pressure from a basic PEEP value (31) with the exhalation valve (11); returning the positive end-expiratory pressure to the basic PEEP value (31) with the exhalation valve (11); and determining an exhalation parameter. The method permits an adaptive change in the expiratory flow during the exhalation. Air trapping can be avoided, and it is possible to respond to changed exhalation parameters within one and the same phase of exhalation.

6 Claims, 3 Drawing Sheets

(51) Int. Cl.
  *A61M 16/00* (2006.01)
  *A61B 5/091* (2006.01)
  *A61M 16/18* (2006.01)
  *A61M 16/22* (2006.01)
  *A61M 16/08* (2006.01)
  *A61M 16/04* (2006.01)

(52) U.S. Cl.
  CPC ........ *A61M 16/0009* (2014.02); *A61M 16/18* (2013.01); *A61M 16/205* (2014.02); *A61M 16/22* (2013.01); *A61M 16/0833* (2014.02); *A61M 2016/003* (2013.01); *A61M 2016/0021* (2013.01); *A61M 2016/0027* (2013.01); *A61M 2016/0036* (2013.01); *A61M 2016/0039* (2013.01); *A61M 2016/0042* (2013.01); *A61M 2016/0413* (2013.01); *A61M 2230/46* (2013.01)

(58) Field of Classification Search
  CPC ...... A61M 2230/46; A61M 2205/3331; A61M 2205/3341; A61M 2205/3344; A61B 5/00; A61B 5/087; A61B 5/091
  USPC .................................................. 128/204.22
  See application file for complete search history.

(56) References Cited

U.S. PATENT DOCUMENTS

| | | | |
|---|---|---|---|
| 5,575,283 A | 11/1996 | Sjoestrand | |
| 5,915,381 A | 6/1999 | Nord | |
| 6,257,234 B1* | 7/2001 | Sun | A61M 16/026 128/204.18 |
| 6,510,851 B2 | 1/2003 | Rydin et al. | |
| 6,564,798 B1* | 5/2003 | Jalde | A61M 16/20 128/200.24 |
| 9,993,604 B2* | 6/2018 | Doyle | A61M 16/026 |
| 2003/0168066 A1* | 9/2003 | Sallvin | A61M 16/205 128/204.21 |
| 2009/0114223 A1* | 5/2009 | Bonassa | A61M 16/024 128/204.23 |
| 2010/0307499 A1* | 12/2010 | Eger | A61B 5/085 128/204.23 |
| 2012/0167884 A1* | 7/2012 | Cardelius | A61M 16/202 128/204.21 |
| 2012/0330177 A1* | 12/2012 | Al-Rawas | A61B 5/091 600/533 |
| 2013/0284177 A1* | 10/2013 | Li | A61M 16/20 128/205.24 |
| 2015/0045687 A1* | 2/2015 | Nakai | A61B 5/085 600/533 |
| 2015/0083135 A1* | 3/2015 | Cheng | A61M 16/0069 128/204.23 |
| 2015/0217069 A1* | 8/2015 | Novotni | A61M 16/20 128/204.23 |
| 2019/0022342 A1* | 1/2019 | Enk | A61M 16/0051 |

* cited by examiner

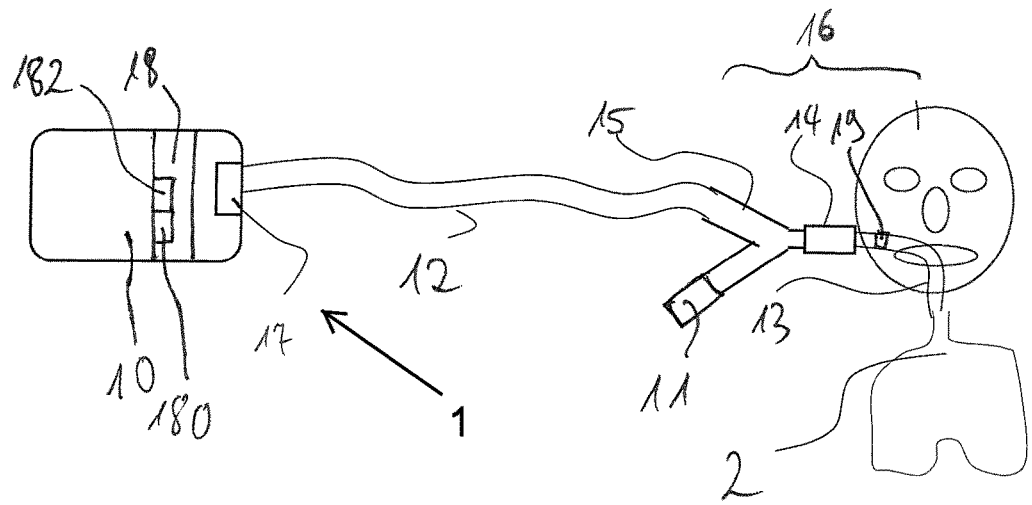
Fig. 1
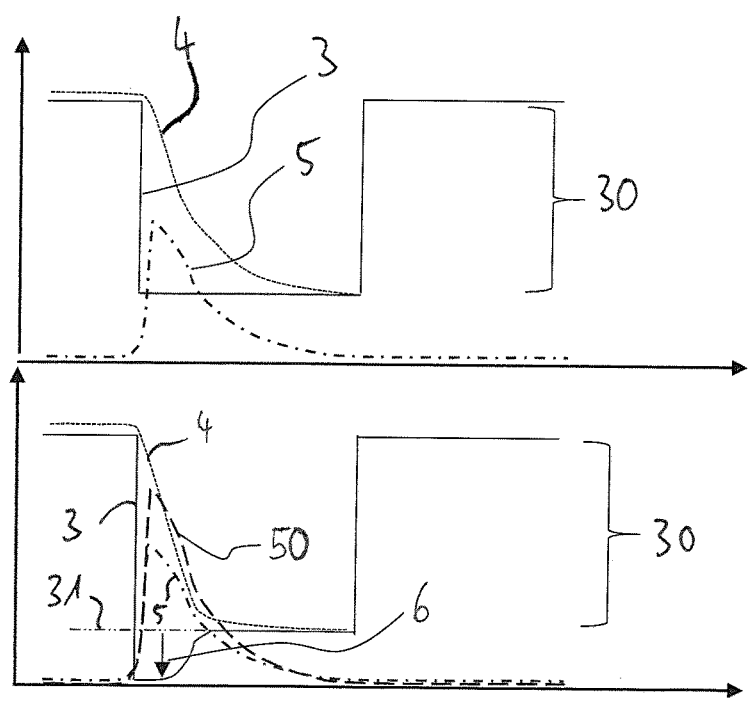
Fig. 2a
Fig. 2b

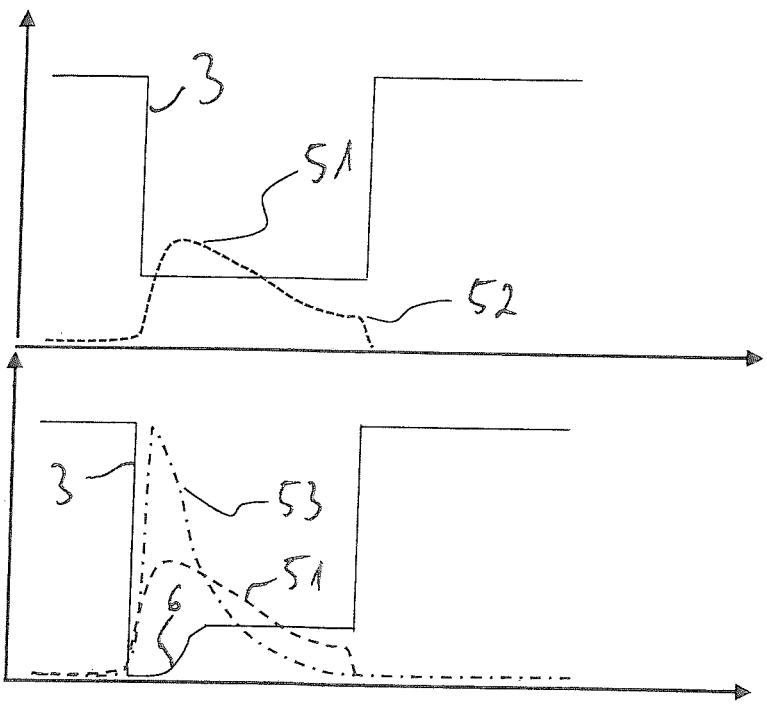
Fig. 3a
Fig. 3b
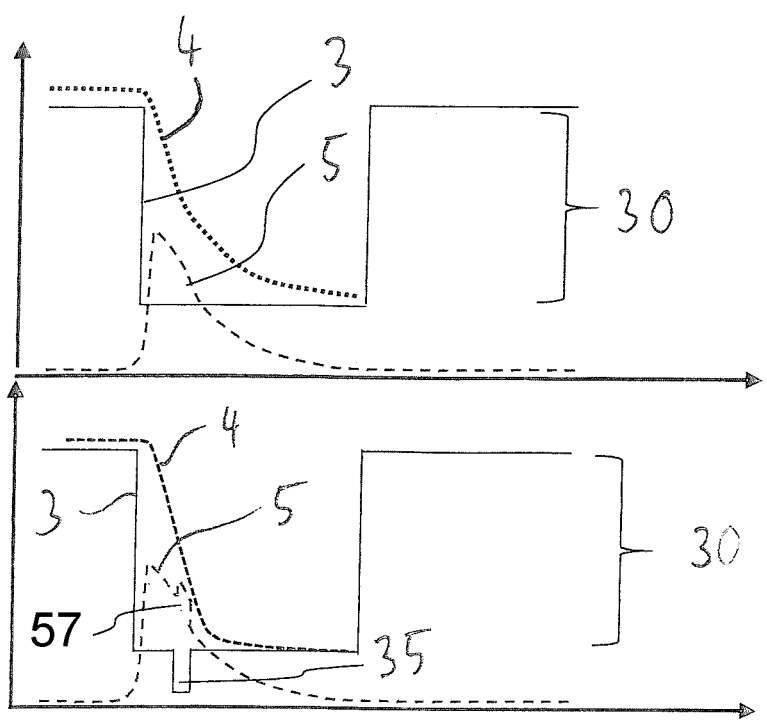
Fig. 4a
Fig. 4b

METHOD AND DEVICE FOR THE ADAPTIVE REGULATION OF A POSITIVE END-EXPIRATORY PRESSURE (PEEP)

CROSS REFERENCE TO RELATED APPLICATIONS

This application claims the benefit of priority under 35 U.S.C. § 119 of German Application 10 2016 012 824.0, filed Oct. 25, 2016, the entire contents of which are incorporated herein by reference.

FIELD OF THE INVENTION

The present invention pertains to a method for controlling expiratory gas flow.

BACKGROUND OF THE INVENTION

Ventilators (also known as respirators) are used to support the ventilation of patients. The ventilators introduce breathing air into the lungs of the patient and also remove the air from the lungs, e.g., in case of mandatory ventilation. In order not to damage the patient's lungs, some parameters of the lungs and of the tube system, with which the breathing air is transported from the device to the patient and optionally back, must be known to the ventilator. Insofar as available, among other things, pneumatic resistances of the device, the compliance of the device, the compliance of the lungs as well as the airway resistance are taken into consideration in this connection.

To avoid collapse of the lungs during the phase of exhalation, a positive end-expiratory pressure (PEEP) is set by means of an exhalation valve, which defines the minimum pressure during the exhalation in the airways of the patient. Since the setting of a positive end-expiratory pressure causes an offset during the pressure stroke for the inhalation, a low PEEP is usually set in the range of 1 mbar to 10 mbar.

Prior-art ventilators take only machine resistances from tubes, valves and other built-in parts (for example, tubes) into account when setting the PEEP. When a ventilator is used to support the exhalation, the pressure cannot be increased, once the PEEP has been set, to compensate additional resistances. If the expiratory flow is too low, an intrinsic PEEP may increase the set PEEP if respiratory minute volumes are to be set as critical volumes. This may lead to so-called air trapping. The total lung volume is not extracted in this case during the exhalation, so that an additional breath volume will be added up in the lungs following each breath. As a result, the pressure continues to increase at the end of the phases of inhalation with continuing breath cycles. This may lead to damage to the respiratory organs of the patient. Furthermore, carbon dioxide is accumulated in the lungs.

Further, ventilators are known, which can generate a sudden, greatly excessive vacuum for a short time in order to enable the patient to have a sort of cough when he or she cannot produce the work of exhalation himself or herself. Air trapping is not avoided in this case, but it can only be reduced by the cough. Furthermore, air trapping is not detected by these ventilators.

It is known from DE 10 2011 106 406 A1 that the PEEP can be caused to follow a predefined course in the phase of exhalation. The PEEP in this case drops from the beginning of the phase of exhalation to the end of the phase of exhalation in order to avoid effects of a pressure regulation in the measured values of carbon dioxide concentrations. Air trapping cannot be avoided with this method either. This is because the residual volume in the lungs cannot be monitored during the exhalation.

In general, the expiratory flow cannot be influenced during the phase of exhalation in prior-art devices, because the exhalation valve and the sensors are separated from the patient due to long gas paths. Changes in the flow of gas are therefore only passed on with a delay or are attenuated by the gas paths, so that the measurement of exhalation parameters simultaneously with changing the PEEP is not possible. The PEEP cannot consequently respond during the detection of changes in the ventilation parameters, which occur above all in case of spontaneous ventilation.

SUMMARY OF THE INVENTION

An object of the present invention is therefore to provide a device and a method that permits an adaptive change in the expiratory flow during exhalation.

The following steps are provided according to the present invention during a phase of exhalation in a method at a user interface of a ventilator, wherein the user interface has an exhalation valve, which provides a positive end-expiratory pressure: Changing the positive end-expiratory pressure from a basic PEEP value by means of the exhalation valve; returning the positive end-expiratory pressure to the basic PEEP value by means of the exhalation valve; and determining an exhalation parameter.

By providing a user interface with an exhalation valve, the exhalation parameters can be determined directly at the user interface, i.e., at the patient. A delay or an attenuation of the pneumatic effects due to long gas paths does not occur. At the same time, it is made possible thereby to measure and to change the exhalation parameters during a single phase of exhalation. By changing the positive end-expiratory pressure during the exhalation, a PEEP adapted to individual conditions is provided. Depending on the demand during the exhalation, a rapid increase and/or a rapid reduction of the expiratory flow can take place due to the change in the PEEP. An adaptive change in the expiratory flow is thus brought about during the exhalation.

A measured actual exhalation parameter can be compared for this with an exhalation parameter set point and the positive end-expiratory pressure can be changed based on the comparison directly in the same exhalation period by means of the exhalation valve, i.e., it can be adapted to the patient's physiological conditions and needs. For example, air trapping during the same phase of exhalation, in which air trapping threatens to develop based on the measured exhalation parameter, can be avoided with the adaptive changing of the PEEP.

The exhalation parameter is advantageously an exhalation resistance. Due to the exact knowledge of the exhalation resistance, the PEEP can be set exactly for the patient. The exhalation resistance acts in connection with the expiratory flow as a minimum pressure, which the patient or the ventilator must overcome for an exhalation. This pressure brings about a minimum PEEP, which can be added to the PEEP set on the device. The PEEP set on the device can be set at a lower value in this manner in order to set up an overall PEEP, which is the sum of the set PEEP and the minimum PEEP.

The averaged exhalation resistance can advantageously be determined over at least two breath cycles. Fluctuations between a plurality of breath cycles can be compensated in this manner. As a result, the PEEP must be set or regulated less frequently. The influence of single-time changes and fluctuations during a breath cycle can thus be diminished.

As an alternative or in addition, the exhalation resistance can advantageously be determined from estimated values from partial exhalation resistances of components in the exhalation path. This estimation may already be carried out before the ventilator is put into operation, so that an exact adaptive regulation of the PEEP can be carried out from the very beginning.

Furthermore, the expiratory gas flow can advantageously be determined and a PEEP can be reduced from the basic PEEP value by a value corresponding to a product of the expiratory gas flow and the averaged exhalation resistance. Air trapping can thus be avoided even more effectively, because a larger expiratory gas flow is brought about based on the lower PEEP value set point than with a higher PEEP.

In another alternative embodiment, the PEEP may be reduced from a first initial value during a phase of exhalation at a predefined time. Further, the PEEP is increased again to the first initial value during the same phase of exhalation. The gas flow is thus determined during the exhalation and a differential exhalation resistance as well as a compliance are further determined from the determined gas flow at the time of the reduction. The state of distension of the lungs and the compliance of the lungs can thus be calculated instead of the tidal volume at which the increase and the reduction of the PEEP occurred.

As an alternative or in addition, a first intrinsic pressure can, furthermore, be determined at the exhalation valve. The PEEP can be increased here from a second initial value during a phase of exhalation at a predefined time. A second intrinsic pressure can then be determined at the exhalation valve. A reduction of the PEEP to the second initial value can take place during the same phase of exhalation after the determination of the second intrinsic pressure at the exhalation valve. Furthermore, a comparison may be carried out between the first intrinsic pressure and the second intrinsic pressure. A plurality of lung parameters can be determined in this manner with a rapid change in the ventilator PEEP. For example, the compliance can be calculated as a change in the volume relative to the pressure. This value can be determined precisely during spontaneous breathing or during assisted ventilation. Since the intrinsic pressure becomes established at the exhalation valve due to the brief interruption in the exhalation flow at the exhalation valve, this may suggest, for example, a high intrinsic overpressure or a high work of exhalation on the part of the patient.

The present invention also pertains to a control device for controlling an exhalation valve, the control device being configured to carry out the above-described method.

Further, a device for controlling an expiratory gas flow in an exhalation path, which device has an exhalation valve at a user interface, which valve provides a positive end-expiratory pressure, and a control device for controlling the exhalation valve, is characterized in that the control device has a determination module for determining an exhalation parameter during a phase of exhalation and a change module for changing the positive end-expiratory pressure during the same phase of exhalation by means of the exhalation valve.

The device may be perfected according to the above-described control device.

The present invention will be described in more detail below on the basis of a preferred exemplary embodiment by means of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic view of a ventilator with an exhalation valve at a user interface;

FIG. 2a is a schematic diagram view showing an increase in the expiratory gas flow;

FIG. 2b is a schematic diagram view showing an increase in the expiratory gas flow;

FIG. 3a is a schematic diagram view showing an initial increase in the expiratory gas flow to avoid air trapping;

FIG. 3b is a schematic diagram view showing an initial increase in the expiratory gas flow to avoid air trapping;

FIG. 4a is a schematic diagram view showing a brief reduction of the PEEP;

FIG. 4b is a schematic diagram view showing a brief reduction of the PEEP;

DESCRIPTION OF THE PREFERRED EMBODIMENTS

Figure 5A:
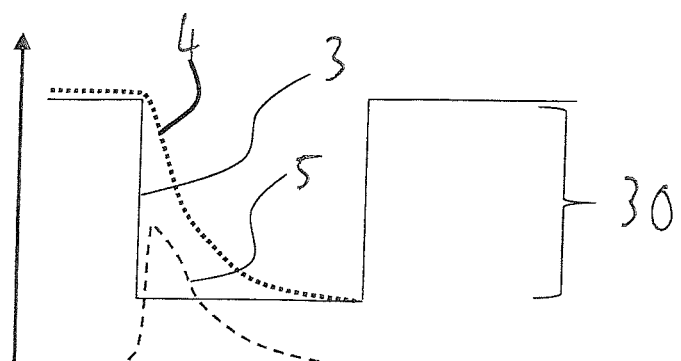
FIG. 5a is a schematic diagram view showing a brief increase in the PEEP.

Referring to the drawings, a ventilator is designated in its entirety by the reference number 1 in FIG. 1. It has a blower unit 10 with a fan 17, which blower unit 10 is connected to a patient 2 via a user interface 16.

The user interface 16 comprises a tube 13, which is connected to a gas flow-measuring unit 14, a Y-piece 15, which is connected with one end to the gas flow-measuring unit 14, and an exhalation valve 11, which is connected to a second end of the Y-piece 15. The last end of the Y-piece 15 is fluid-communicatingly connected to a fan 17 of the blower unit 10 via a tube 12.

As an alternative, the user interface 16 may be configured as a mask, as a nasal mask or also in another form, the user interface 16 always comprising an exhalation valve 11.

The ventilator 1 further comprises a control device 18, which transmits control signals to the exhalation valve 11 and to the fan 17, as well as received measured signals from the gas flow-measuring unit 14. The control device 18 determines the expiratory gas flow on the basis of the measured data of the gas flow-measuring unit 14. The control device 18 controls the exhalation valve 11 during the phase of exhalation on the basis of the data of the gas flow-measuring unit 14. Further, the control device 18 can actuate the exhalation valve 11 during a phase of exhalation with predefined maneuvers and then detect the change in the expiratory gas flow in the same phase of exhalation by means of the gas flow-measuring unit 14.

The control device 18 comprises for this a change module 182, which transmits change signals to the exhalation valve 11. The change signals cause the exhalation valve 11 to set a PEEP deviating from a basic PEEP value 31.

To detect the measured signals of the gas flow-measuring unit 14, the control device 18 has a determination module 180. The determination module 180 is further configured to receive pressure signals from pressure sensor 19. The determination module 180 can determine additional parameters, e.g., the exhalation resistance, from the transmitted signals.

A plurality of exhalation parameters are plotted over time in FIG. 2a. The rectangular curve drawn in solid line presents the exhalation valve pressure 3 over time. A high exhalation valve pressure 3 shows a phase of inhalation, while a low exhalation valve pressure 3 indicates a phase of exhalation. The exhalation valve pressure 3 is not 0 mbar during the phase of exhalation, but it amounts to a few mbar, which corresponds to the PEEP. The difference between the maximum and the minimum of the exhalation valve pressure 3 is the first pressure difference 30. The minimum of the exhalation valve pressure 3 in FIG. 2a corresponds to the basic PEEP value 31.

The airway pressure 4, which becomes established in the lungs of the patient 2, is represented by the broken line. The airway pressure 4 drops markedly more slowly than the exhalation valve pressure 3 from a maximum during the phase of exhalation to the PEEP.

Further, a first expiratory gas flow 5, which designates the gas flow during the phase of exhalation, is shown by the dash-dot line. The first expiratory gas flow 5 drops to 0 L/sec at the end of the phase of exhalation from a maximum at the beginning of the phase of exhalation. The exhalation valve pressure 3 is controlled by the control unit 18. The first expiratory gas flow 5 is determined by the gas flow-measuring unit 14.

FIG. 2b shows the first expiratory gas flow 5 as a reference in order to illustrate the differences from the second expiratory gas flow 50 described below. Furthermore, the basic PEEP value 31 is drawn as a double dash-dot line to illustrate the differences. The exhalation valve pressure 3 is reduced by a PEEP pressure reduction 6 at the beginning of the phase of exhalation. As a result, the expiratory gas flow is increased, as is indicated by the broken line, which shows the second expiratory gas flow 50. The airway pressure 4 now drops more rapidly than in FIG. 2b. As soon as the control device 18 determines that the airway pressure 4 threatens to drop below the basic PEEP value 31, the exhalation valve pressure 3 is raised again to the basic PEEP valve 31. The drop of the airway pressure 4 takes place more slowly than before beginning from the rise, because the expiratory gas flow is reduced by the rise in the exhalation valve pressure 3.

It is possible in this manner to achieve an increase in the expiratory gas flow 50 at the beginning of the phase of exhalation without the airway pressure 4 of the patient 2 dropping below the PEEP that is meaningful from a physiological point of view.

Knowing the time curve of the airway pressure 4, the airway resistance of the system comprising the ventilator 1 and the patient 2 can be calculated. Further, the compliance of the system can be calculated. The PEEP can be set at the exhalation valve 11 accurately by means of the calculated values by the control device 18 during the same phase of exhalation. The pressure at the exhalation valve 11 may be lower in this case than the desired PEEP, because the PEEP is calculated from the pressure at the exhalation valve 11 in combination with the pressure that is calculated from the expiratory gas flow multiplied by the exhalation resistance.

The averaged exhalation resistance of the system from a plurality of breaths can be used as a basis for the calculation of the optimal pressure at the exhalation valve 11 in order to suppress dynamic changes between different breaths.

In an alternative embodiment, the exhalation resistance can also be estimated with sufficient accuracy in case of known components. The exhalation resistance should be estimated rather as too low than as too high in order not to risk a PEEP that is too low for the patient 2.

FIG. 3a shows a situation in which the expiatory gas flow is not sufficient during the phase of exhalation to allow the entire breath volume to flow out of the lungs during the phase of exhalation. The phase of inhalation thus starts too early. The expiratory gas flow is designated here as the third expiratory gas flow 51, which is relatively low and has a flat course compared to the first expiratory gas flow 5 shown in FIG. 2a. An air trapping indication 52 can be seen at the end of the phase of exhalation. The air trapping indication 52 arises from the fact that the expiratory gas flow 51 does not drop to 0 L/sec at the end of the phase of exhalation but remains at a value greater than 0 L/sec. This indicates that the PEEP was estimated to be too high or the exhalation resistance is higher than assumed.

Air remains in the lungs of the patient 2 after each phase of exhalation due to the air trapping. In ventilation modes in which the respiratory minute volume is maintained at a constant value during the inhalation, the same volume is introduced into the lungs of the patient 2 during each phase of inhalation. Due to the air trapping, there remains an offset, which increases with each breath, after each phase of exhalation, so that the residual volume in the lungs increases with each phase of inhalation.

FIG. 3b shows a maneuver that corresponds to the maneuver in FIG. 2b, and air trapping is avoided according to FIG. 3b. The exhalation valve pressure 3 is reduced for this to far below the desired PEEP at the beginning of the phase of exhalation. This is represented by the PEEP pressure drop 6. There is a fourth expiratory gas flow 53 during this time, which rapidly transports the breath volume from the lungs. The third expiratory gas flow 51, which is markedly lower at the beginning of the phase of exhalation than the fourth expiratory gas flow 53, is additionally shown for comparison. Further, the fourth expiratory gas flow 53 drops markedly below the first expiratory gas flow 51 at the end of the phase of exhalation. As soon as the airway pressure 4, which is not shown in FIG. 3b, threatens to drop below the PEEP, the exhalation valve pressure 3 is again raised to the basic PEEP value 31. As can be seen in FIG. 3b, the fourth expiratory gas flow 53 drops to 0 L/sec at the end of the phase of exhalation, so that the lungs were completely freed of the breath volume. Air trapping is avoided hereby.

Like FIG. 2a, FIG. 4a shows a reference curve, which is used to illustrate the differences of the curves shown in FIG. 4b.

FIG. 4b shows an embodiment of the method with which the differential value can be calculated for the exhalation resistance and the compliance at the tidal volume or state of distension of the lungs that are present at this time. The exhalation valve pressure 3 is briefly reduced for this within a pressure reduction period 35. The pressure reduction period 35 is very short relative to the entire phase of exhalation. It may be in the range of 10-30 msec.

Due to the brief reduction of the exhalation valve pressure 3, the first expiratory gas flow 5 is briefly increased with an expiratory gas flow increase 57. Due to the drop of the PEEP during the pressure reduction period 35, the pressure at the exhalation valve 11 corresponds to the product of the expiratory gas flow times the exhalation resistance at this point of the tidal volume. The particular exhalation resistance can therefore be determined in this manner at different points of the tidal volume, i.e., for different states of distension of the lungs. Further, the compliance can thus be determined as a function of the tidal volume of the lungs.

Like FIGS. 2a and 4a, FIG. 5a shows a reference diagram.

Figure 5B:
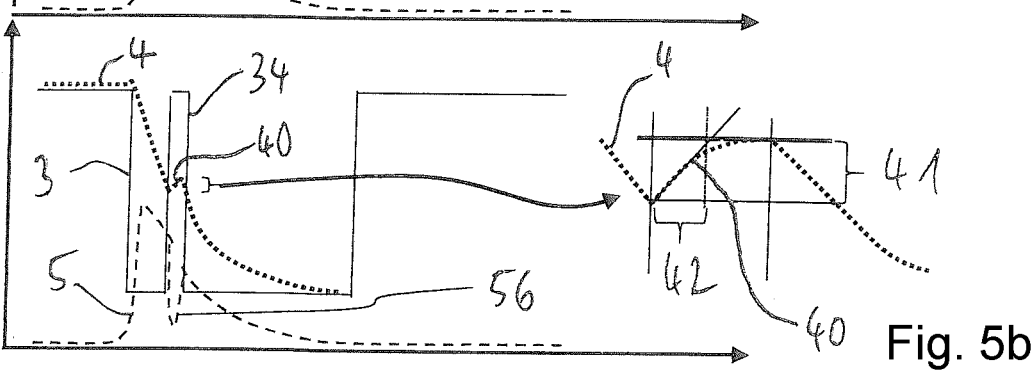
FIG. 5b is a schematic diagram view showing a brief increase in the PEEP.

FIG. 5b shows an arbitrary brief interruption of the first expiratory gas flow 5, which is due to the exhalation valve pressure 3 being briefly raised to the inhalation pressure within a pressure increase period 34. An airway pressure increase 40 now becomes established based on the briefly reduced expiratory gas flow 56. The compliance of the lungs can be calculated based on the rise (in airway pressure 40) during the measurement period 42 and by means of the airway pressure difference 41.

This method is suitable above all for a measurement of the compliance during spontaneous breathing or assisted ventilation. It was impossible or difficult to determine the compliance during spontaneous breathing or assisted ventilation before.

The shorter the pressure increase period 34, the more accurately can the compliance be determined for a defined tidal volume, because the respiratory parameters differ only slightly before and after the pressure increase period 34 based on the only brief change in the exhalation valve pressure 3.

If a major airway pressure difference 41 develops, there may an indication of a high intrinsic overpressure in the lungs or of a high active work of exhalation on the part of the patient 2. Both represent important information in relation to the ventilation situation and a possible exhaustion and hence an unsuccessful weaning from the ventilator (weaning).

While specific embodiments of the invention have been shown and described in detail to illustrate the application of the principles of the invention, it will be understood that the invention may be embodied otherwise without departing from such principles.

What is claimed is:

1. A method for controlling an expiratory gas flow at a user interface of a ventilator, wherein the user interface has an exhalation valve to provide a positive end-expiratory pressure (PEEP), the method comprising the steps of:
   during a phase of exhalation, changing, with the exhalation valve, the positive end-expiratory pressure (PEEP) from a basic PEEP value to another PEEP value;
   during said phase of exhalation, returning, with the exhalation valve, the positive end-expiratory pressure (PEEP) to the basic PEEP;
   during said phase of exhalation, determining total exhalation resistance values at points in time of said phase of exhalation;
   providing a plurality of patient exhalation resistance values based on an estimate of partial exhalation resistance of components in an exhalation path of the ventilator and each of the determined total exhalation resistance values; and
   during said phase of exhalation, determining the expiratory gas flow, wherein the step of changing the positive end-expiratory pressure (PEEP) from the basic PEEP value to another PEEP value comprises reducing the PEEP from the basic PEEP value by a product of the expiratory gas flow times one of the plurality of provided patient exhalation resistance values corresponding in time to the determined expiratory gas flow.

2. A method in accordance with claim 1, further comprising:
   during said phase of exhalation determining a first intrinsic pressure at the exhalation valve;
   subsequent to said step of determining the first intrinsic pressure increasing the PEEP from an instantaneous value by means of the exhalation valve at a predefined time during said phase of exhalation;
   subsequent to said step of increasing the PEEP from the instantaneous value determining a second intrinsic pressure at the exhalation valve; and
   comparing the first intrinsic pressure and the second intrinsic pressure to determine one or more lung parameters.

3. A method in accordance with claim 2, wherein lung the one or more lung parameters determined by comparing the first intrinsic pressure and the second intrinsic pressure is lung compliance, wherein wherein the determination of the lung compliance comprises calculating a change in gas volume relative to a change in pressure.

4. A control device for controlling an exhalation valve at a user interface of a ventilator, wherein the control device is configured to carry out a method comprising the steps of:
   during a phase of exhalation, changing, with the exhalation valve, the positive end-expiratory pressure (PEEP) from a basic PEEP value to another PEEP value;
   during said phase of exhalation, returning, with the exhalation valve, the positive end-expiratory pressure (PEEP) to the basic PEEP;
   during said phase of exhalation, determining total exhalation resistance values at points in time of said phase of exhalation;
   providing a plurality of patient exhalation resistance values based on an estimate of partial exhalation resistance of components in an exhalation path of the ventilator and each of the determined total exhalation resistance values; and
   during said phase of exhalation determining an expiratory gas flow, wherein the step of changing the positive end-expiratory pressure (PEEP) from the basic PEEP value to another PEEP value comprises reducing the PEEP from the basic PEEP value by a product of the expiratory gas flow times one of the plurality of provided patient exhalation resistance values corresponding in time to the determined expiratory gas flow.

5. A device for controlling an expiratory gas flow in an exhalation path of a ventilator, the device comprising:
   a user interface;
   an exhalation valve at the user interface, the exhalation valve providing a positive end-expiratory pressure (PEEP);
   a gas flow-measuring unit at the user interface; and
   a control device configured to control the exhalation valve, wherein the control device comprises:
   a determination module configured to: determine the expiratory flow based on measured data of the gas-flow measuring unit, and determine total exhalation resistance values at points in time of said phase of exhalation and provide a plurality of patient exhalation resistance values by subtracting an estimate of partial exhalation resistance of components in an exhalation path of the ventilator from each of the determined total exhalation resistance values;
   a change module configured to change the positive end-expiratory pressure (PEEP) during said phase of exhalation with the exhalation valve, wherein the change to the positive end-expiratory pressure comprises reducing the PEEP from the basic PEEP value by a value corresponding to a product of the determined expiratory gas flow times and one of the plurality of provided patient exhalation resistance values corresponding in time to the determined expiratory gas flow.

6. A device in accordance with claim 5, wherein the control device is configured to carry out a method comprising the steps of:
- during said phase of exhalation, changing, with the exhalation valve, the positive end-expiratory pressure (PEEP) from the basic PEEP value to another PEEP value;
- during said phase of exhalation, returning, with the exhalation valve, the positive end-expiratory pressure (PEEP) to the basic PEEP;
- during said phase of exhalation, determining an exhalation parameter comprising an exhalation resistance; and
- during said phase of exhalation determining expiratory gas flow, wherein the step of changing the positive end-expiratory pressure (PEEP) from the basic PEEP value to another PEEP value comprises reducing the PEEP from the basic PEEP value by a product of the expiratory gas flow times and one of the plurality of provided patient exhalation resistance values corresponding in time to the determined expiratory gas flow.

* * * * *